United States Patent [19]

Taumann et al.

[11] 4,220,866
[45] Sep. 2, 1980

[54] ELECTRON APPLICATOR

[75] Inventors: Leonhard Taumann; Edgar B. Symmons, both of Walnut Creek, Calif.

[73] Assignee: Siemens Aktiengesellschaft, Berlin & Munich, Fed. Rep. of Germany

[21] Appl. No.: 871,200

[22] Filed: Jan. 21, 1978

[30] Foreign Application Priority Data

Dec. 30, 1977 [DE] Fed. Rep. of Germany ....... 2759073

[51] Int. Cl.$^2$ .......................... G21F 5/04; G21K 1/04
[52] U.S. Cl. .................................... 250/513; 250/511
[58] Field of Search ............... 250/505, 510, 511, 512, 250/513, 514, 401, 402

[56] References Cited

U.S. PATENT DOCUMENTS

| | | | |
|---|---|---|---|
| 2,542,196 | 2/1951 | Haupt | 250/511 |
| 3,863,073 | 1/1975 | Wagner | 250/402 |
| 3,942,019 | 3/1976 | Claridge et al. | 250/512 |
| 4,034,228 | 4/1977 | Arauner | 250/511 |
| 4,053,808 | 10/1977 | Peacock | 250/512 |

Primary Examiner—Craig E. Church
Assistant Examiner—Thomas P. O'Hare
Attorney, Agent, or Firm—Hill, Van Santen, Steadman, Chiara & Simpson

[57] ABSTRACT

In the illustrated embodiment, an electron collimator is to be mounted on the accessory holder of an electron accelerator. In radiation therapy, the down beam end of the applicator is to contact the patient to establish a precise spacing of the electron source therefrom. The legs of the L-shaped collimator plates have rods secured to the corner part thereof which link pairs of overlapping legs to a common carrier for joint lateral adjustment toward and away from the beam axis. The rods slide in apertures in the carrier as the legs are adjusted longitudinally. Cornered wall elements are secured to each collimator plate and overlap each other to surround the beam path, and have in-turned closely overlapping edges which terminate flush with the inner margins of the collimator plates so as to provide further electron collimation and to provide an essentially smooth patient contacting end face.

12 Claims, 2 Drawing Figures

ELECTRON APPLICATOR

BACKGROUND OF THE INVENTION

The invention relates to an electron applicator intended for use at the location of radiation egress in the radiation direction behind the primary collimator of an electron accelerator, the applicator providing a plurality of overlapping, reciprocally adjustable wall elements, and a plurality of collimator plates disposed in planes aligned perpendicularly relative to the symmetry axis of the electron applicator.

During irradiation with electrons, on account of the scattering of the electrons in air, it is common in medical radiation therapy to shield off the electron beam cone, issuing from the electron accelerator, by means of an electron applicator which surrounds the axis of the electron beam at an intermediate space between the beam defining system (or radiator head) of the electron accelerator and the patient. For this purpose, it is known to secure to the accessory holder of the beam defining system fixed conical electron applicator tubes adapted in shape to the field which is to be irradiated. These electron applicator tubes are brought into direct contact with the patient. They have the additional function of determining the spatial interval between the patient and the beam defining system which must be adhered to with a high degree of precision for the dose calculation.

In order to also be able to utilize electron applicators of this type in the case of radiation fields of varying sizes, a construction of the walls of such an electron applicator from angled mutually overlapping wall elements is known from the U.S. Letters Pat. No. 3,942,019. However, it is considered a disadvantage here that adjustment mechanisms must be mounted at the four corners of the electron applicator, which adjustment mechanisms are connected with the angled wall elements, and which are coupled together in pairs, respectively, via gear rods in order to avoid canting effects. These adjustment mechanisms with the longitudinally extending gear rods widen (or enlarge) the dimensions of the electron applicator on the patient and impede a close fit (or contacting) of the same on the body of the patient. In addition, it is disadvantageous in the case of an electron applicator for the conventional inner edges of the applicator walls, which edges are provided at the patient-end, and which bring about an additional collimation of the cone of rays, must overlap one another. On account of the wall thickness of these edges, which is required for shielding purposes, a close fit (or contacting) on the patient, such as is still possible in the case of fixed applicator tubes, is thus prevented.

From the U.S. Letters Pat. No. 4,034,228, an electron applicator is disclosed which is adjustable in its external dimensions, and which does not require adjustment mechanisms at the patient-end. However, in the case of this applicator, the considerable technical outlay required for the adjustment of the applicator walls is a disadvantage. However, even in the case of this electron applicator, the edges of the wall elements, which additionally again sharply collimate the cone of rays on the patient-end of the applicator, impede a close fit (or contacting) on the patient.

SUMMARY OF THE INVENTION

The object which is the basis of the invention consists in developing an adjustable electron applicator adaptable to varying field sizes which can be manufactured at a favorable cost while also affording to close fit (or contacting) on the body of the patient.

Therefore, in accordance with the invention, the collimator plates of an electron applicator of the type initially cited manifest an angular layout, overlap one another at the ends of their legs, and each of said plates is displaceably mounted, for movement in directions along the length of both their legs, by means of carriers which are perpendicularly adjustable relative to the direction of the symmetry axis. This construction provides the great advantage that no adjustment mechanisms whatsoever are required at the patient-end of the electron applicator, and that the adjustment mechanism of the electron applicator is nontheless comparatively simple.

In an expedient further development of the invention, the mutually overlapping legs of two adjacent collimator plates, respectively, can be displaceably mounted by means of a common carrier. This type of construction makes coupling rods between the individual adjustment mechanisms of the adjacent collimator plates unnecessary, since when a carrier is adjusted, both collimator plates, controlled from the same side of the electron applicator, are, in this manner, automatically jointly adjusted.

The properties of collimation of the applicator can be improved if all the collimator plates of the electron applicator, in accordance with the invention, are positioned alternately in two parallel directly adjacent planes. By this means, the difference in level of the collimation at the patient-end is restricted to the thickness of the collimator plates. In addition, the contacting (or fittig) properties on the patient are thus simultaneously somewhat improved.

The support mounting of the collimator plates can be simplified if, in accordance with the invention, each of the collimator plates is provided with two sliding rods aligned in parallel with both their legs. The sliding rods are guided in a longitudinally displaceable fashion each in one bore, respectively, of the associated carrier. The advantage of this is that, in order to support the collimator plates, the carriers need be provided with only two superimposed bores at their end bearing the collimator plates.

In a particularly advantageous embodiment of the invention, the carriers of the collimator plates can be displaceably mounted perpendicularly to the direction of the symmetry axis on an applicator frame or plate which can be inserted into the accessory holder of the electron accelerator. The utilization of an applicator frame or plate such as this serving as the common carrier of the individual constructional units of the electron applicator not only facilitates the construction of the applicator, but also facilitates its insertion into the accessory holder of an electron accelerator. At the same time, through adaptation of the external dimensions of the applicator frame or plate to the guidance means of the accessory holder, the prerequisite has been provided for the transmission, with simple means, of information from the electron applicator to the electron accelerator, and conversely.

In a particularly advantageous futher development of the invention, one cornered wall element can, in each instance be mounted onto each of the angled collimator plates, said wall element partially covering the three external walls or sufaces of the electron applicator which border on the respective angled collimator plate. The advantage associated herewith consists in that the scatter electrons occurring in the region of the patient surface as well as in the region of the collimator plates are shielded by means of the wall elements.

In a further particularly advantageous embodiment of the invention, the bent (or curved) in edges of each wall element, on the end not facing the radiation source but facing the symmetry axis, can close flush with the associated collimator plate and be fixedly connected with said collimator plate with the object of producing a supportive collimation of the cone of rays. This has the advantage that the wall elements are not only utilized for the purpose of radiation shielding, but also for the purpose of producing a sharper collimation.

At the same time the prerequisite has been provided for achieving an improved fit (or contacting) of the electron applicator on the patient.

The fit (or contacting) on the patient can be significantly improved if the adjacent wall elements, particularly on the side not facing the radiation source, overlap one another in a nearly grazing fashion. The electron applicator, with its bent (or curved) in wall elements can thus be brought to a close fit on the body of the patient; i.e., without any appreciable gradation whatsoever. Since these wall elements manifest only a minimal wall thickness and grazingly overlap one another, virtually no notable gradations of consequence occur at those locations at which they overlap. The otherwise laterally issuing scatter electrons are thus substantially reduced.

Additional details of the invention shall be explained in greater detail on the basis of a sample embodiment illustrated in the figures; and other objects, features and advantages will be apparent from the detailed description taken in connection with the accompanying sheets of drawings.

DETAILED DESCRIPTION

Figure 1:
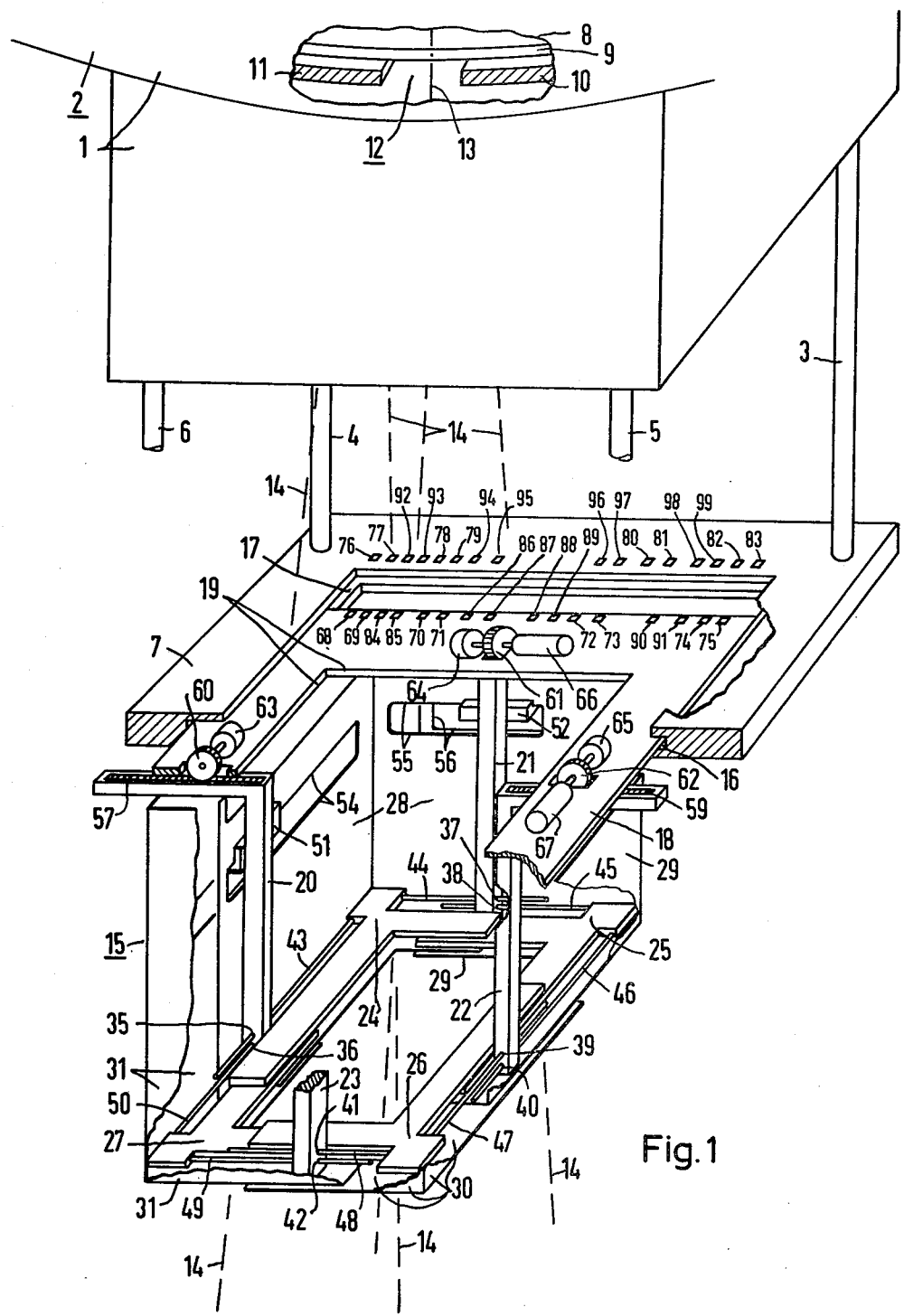
FIG. 1 is a partial perspective view which illustrates the beam-defining system of an electron accelerator with an accessory holder (which has portions thereof broken away and in section), and an inventive electron applicator (also shown partly broken away and in section) partly inserted into the accessory holder.

In FIG. 1, the beam defining system (or radiator head) 1 of an electron accelerator 2 is apparent and, at a spatial interval therefrom, an accessory holder 7 mounted via four columns 3, 4, 5, 6 to said beam defining system 1. A wall of the housing for system 1 has been broken away at 8 to indicate beam defining components such as 9, 10, 11 or a primary collimator 12. The accessory holder 7 is centered relative to the symmetry axis 13 of the primary collimator 12, which, during symmetric collimation coincides with the central ray of the issuing cone of rays 14. In the illustration of FIG. 1, an inventive electron applicator 15 has portions of its walls broken away. The applicator 15 is shown inserted only three fourths of the way into the guide means 16, 17 of the accessory holder 7. The electron applicator 15 is mounted on a frame-shaped applicator plate 18 which is adapted in its external dimensions to the dimensions of guide means 16, 17 of accessory holder 7. The inner opening 19 of applicator plate or frame 18 is kept somewhat greater in its dimensions than the maximum cone of rays 14 which can be defined by collimator 12.

Figure 2:
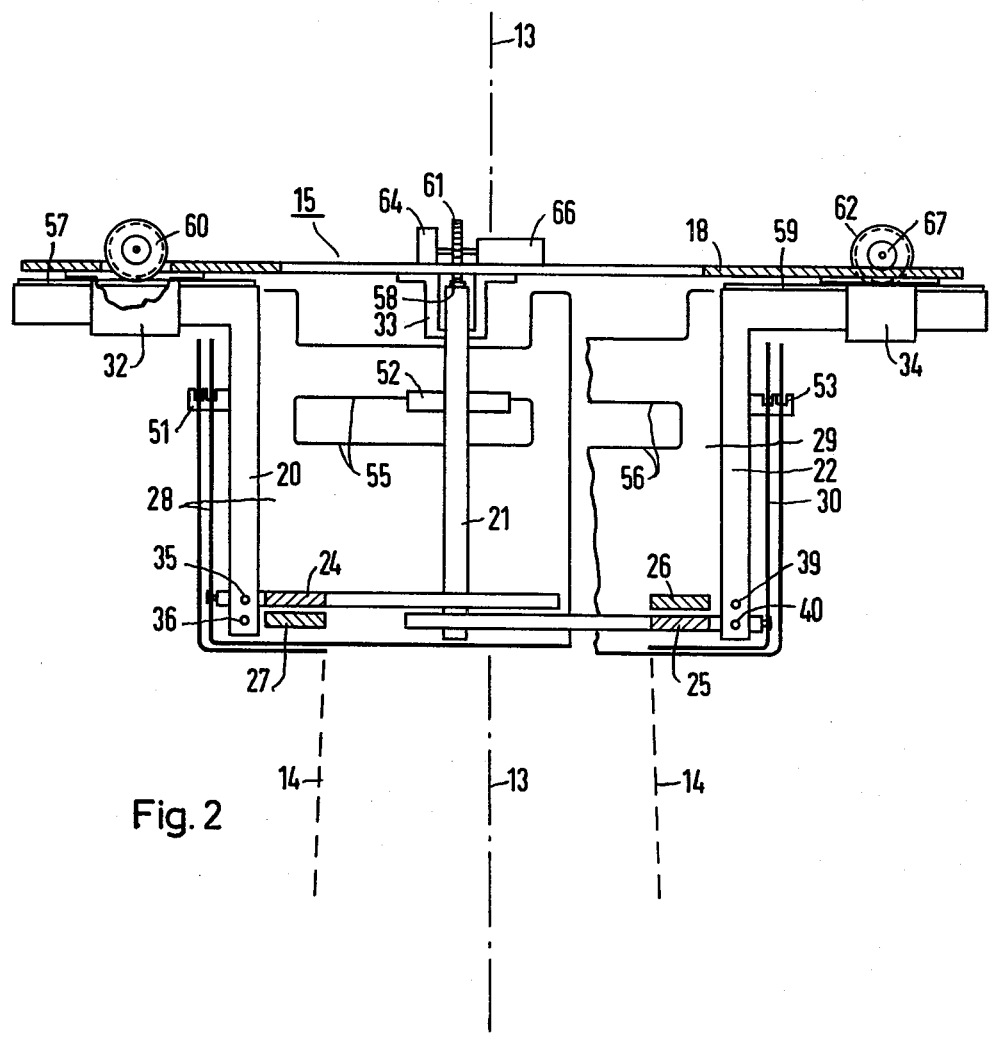
FIG. 2 illustrates an enlarged longitudinal sectional view of the electron applicator of FIG. 1.

In the center of each of the four frame-sides of applicator plate 18, angle-shaped carriers 20, 21, 22, 23 for the collimator plates 24, 25, 26, 27 and the wall elements 28, 29, 30, 31 of the electron applicator 15 are displaceably mounted perpendicularly to the symmetry axis of the electron applicator in guide bushings such as 32, 33, 34, (FIG. 2). Carriers 20, 21, 22, 23 are provided with two bores 35 through 42 each at their end not facing beaming defining system 1. Guide rods 43 through 50 are guided in these bores. Two of these guide rods in each instance are secured to the exterior corners of each one of the angularly constructed collimator plates 24, 25, 26, 27. For example, as seen at the lower left in FIG. 1, one end of guide bars 49 and 50 is secured to the corner of L-shaped collimator plate 27. The guide rods 43 through 50 extend parallel to the two legs of the respective collimator plate to which they are secured. Guide shoes such as 51, 52, 53 for guiding the wall elements 28, 29, 30, 31 of the electron applicator 15 are mounted on the carriers 20, 21, 22, 23 between the bores for the guide rods and frame or plate 18. Wall elements 28, 29, 30, 31 are essentially provided with an angular construction and extend parallel to the legs of one collimator plate in each instance over the greater portion of two adjacent lateral walls of electron applicator 15. In addition, they are bent (or curved) in on the side of the electron applicator not facing beam defining system 1 but facing the patient, and, at this patient end, they project into the clear opening of electron applicator 15 as far as the respective collimator plates 24, 25, 26, 27. To this end, they are each respectively fastened to the corner of the collimator plate extending over the same section of the applicator. In addition, in the central region of each wall surface, the wall elements are provided with an elongated slot such as 54, 55, 56 (only three visible). The upper edge of each slot slides on the guide shoe (such as 52, FIG. 2) of the carrier (such as 21) associated. In FIG. 2, lateral walls 28 and 29 are shown as having slots 55 and 56. These slots are guided in respective grooves of guide shoe 52. Note the grooves shown in guide shoes 51 and 53, FIG. 2.

The legs of carriers, 20, 21, 22, 23, which extend parallel to the applicator plate 18 bear, on their side facing tube plate 18, a toothed rack such as 57, 58, 59 which meshes with a pinion such as 60, 61, 62 rotatably mounted on frame or plate 18. A potentiometer such as 63, 64, 65 (only three illustrated) as well as a servo motor such as 66, 67 (only two illustrated), are coupled with the respective pinions. The electrical terminals of the potentiometers are connected to contacts 68, 69, 70, 71, 72, 73, 74, 75, which are mounted on the front edge of applicator plate 18 (as viewed in the direction of insertion of frame 18 into accessory holder 7 of the beam defining system 1 of electron accelerator 2). There are associated with these contacts corresponding counter-contacts 76, 77, 78, 79, 80, 81, 82, 83 on the accessory holder 7. The control circuit (not illustrated) of the primary collimator 12 is connected to these counter contacts 76-83. In addition to contacts 68 through 75 of potentiometers such as 63, 64, 65, additional contacts 84 through 91 for the servo motors such as 66, 67 (only two illustrated) associated with the carriers 20, 21, 22, 23, are mounted onto the front edge of application plate 18 (viewed in the direction of insertion). Additional counter-contacts 92-99 in the accessory holder are associated with the servo motors.

By inserting the electron applicator 15 into accessory holder 7 of the beam defining system 1 of electron accelerator 2, contacts 68 through 75 of potentiometers such as 63, 64, 65, as well as additional contacts 84 through 91 of servo motors such as 66, 67, are brought into contact with the corresponding counter contacts 92-99 of accessory holder 7. Now the servo motors such as 66, 67 of the electron applicator can be actuated via the control panel (not illustrated) of the electron accelerator 2. Upon actuation of a servo motor, the latter displaces a toothed rack such as 57, 58, 59, of the corresponding carrier 20, 21, 22, 23, as a result of the rotation of the pinion such as 60, 61, 62. There are entrained with the carrier the two guide rods 43 through 50 of the two collimator plates 24 through 27, whose legs overlap on the side of the corresponding carrier. At the same time, the respectively different guide rods of these two collimator plates slide in the bores 35 through 42 of the carriers of the adjacent sides. The wall elements 28 through 31, which are fastened at the edges of the electron applicator, together with the corner of one collimator plate, respectively, are supported with their upper edges of their two openings 54, 55, 56, on the guide shoes 51 through 53 of the carriers. They overlap one another in all positions of the electron applicator with the least possible mutual spacing. Since they are bent (or curved) in at the end of the electron applicator facing the patient, and project into the clear opening of the electron applicator precisely as far as the collimator plates 24, 25, 26, 27, said wall elements reinforce the collimation (electron absorbing) effect of said collimator plates. Due to their thin wall thickness and their mutual small interspacing, gradations result at the overlapping zones which amount to only a few millimeters in height, said gradations presenting virtually no obstacle to the close fit of the electron applicator 15 on the body of the patient. Accordingly, with this electron applicator, every symmetric and asymmetric rectangular field-collimation can be precisely adjusted.

Pursuant to adjustment of carriers 20, 21, 22, 23, by means of servo motors such as 66, 67, the potentiometers such as 63, 64, 65, coupled with the pinions such as 60, 61, 62 are jointly adjusted. The respective resistance values of the individual potentiometers 63, 64, 65, which are read-off at the accessory holder 7, can be compared in a Wheatstone bridge circuit with the setting values of the primary collimator plates such as 9, 10, 11 of primary collimator 12, said adjustment values being read-off in the same manner. Only when the positions (or settings) of the potentiometers of the electron applicator and of the primary collimator correspond; i.e. when the diagonal voltage of the Wheatstone bridge is zero, can the current supply of electron accelerator 2 be released (or triggered) via a switching element incorporated in the diagonal of the bridge circuit. It is thereby guaranteed that the irradiation can only be switched on when the primary collimator 12 is adjusted such that it reinforces the collimation of electron applicator 15.

In another modification of the invention, it is also possible to connect the potentiometers of the electron applicator to one follow-up control each for the primary collimator plates such as 9, 10, 11 of primary collimator 12, such as is already prior knowledge e.g. from the U.S. Letters Pat. No. 2,921,202, particularly the fifth and sixth figures thereof. The follow-up control could also be realized in a digital fashion such as is disclosed in the German Offenlegungsschrift 24 40 146, corresponding to U.S. Ser. No. 604,079 now U.S. Pat. No. 4,049,967, for the follow-up control of the scale. The utilization of a follow-up control provides the result that the primary collimator plates such as 9, 10, 11 of beam defining system 1 are adjusted synchronously with the corresponding collimator plates of electron applicator 15. In this instance, also, primary collimator 12 reinforces the collimation of the electron applicator 15 in all collimation settings.

It will be apparent that many modifications and variations may be effected without departing from the scope of the novel teachings and concepts of the present invention.

I claim as my invention:

1. An electron irradiator comprising an electron source, primary electron field shaping means and an electron applicator at the point of radiation egress in the radiation direction after the primary field shaping means of the electron source, said adjustable collimator plates surrounding and disposed in planes oriented perpendicularly to the symmetry axis of the electron applicator, characterized in that the collimator plates (24, 25, 26, 27) each have transverse legs which overlap the legs of other plates, said collimator plates each having fixedly connected guide rods extending parallel to the respective legs, and the length of each of the guide rods being such as to not extend beyond the ends of a respective parallel leg movable therewith, and carrier means (20, 21, 22, 23) mounting each of said collimator plates for movement along the directions of the lengths of both its legs, said carrier means (20, 21, 22, 23) being adjustable toward and away from the symmetry axis (13), each of the collimator plates (24, 25, 26, 27) having mounted therewith one cornered wall element (28, 29, 30, 31) partially covering the exterior walls of the electron applicator (15) which border on the respective collimator plate, said wall elements being opaque to electrons and being substantially parallel to said symmetry axis and adjacent wall elements (28, 29, 30, 31) overlapping in a virtually grazing fashion on the side remote from the electron source (2), the guide rods being slideably attached to and guided by respective carrier means during adjustment of the carrier means without projection of the guide rods outside of the wall elements.

2. An electron applicator according to claim 1, characterized in that the overlapping legs of adjacent collimator plates, respectively (24, 25, 26, 27), are displaceably mounted by a common carrier of said carrier means (20, 21, 22, 23).

3. An electron applicator according to claim 1, characterized in that all collimator plates (24, 25, 26, 27) of the electron applicator tube (15) are alternately mounted in two parallel, directly adjacent planes.

4. An electron applicator according to claim 1, characterized in that each collimator plate (24, 25, 26, 27) has two guide rods (43 through 50) oriented parallel to its legs, which are guided in a longitudinally displaceable fashion in one bore each (35 through 42) of the carrier means (20, 21, 22, 23).

5. An electron applicator according to claim 1, characterized in that the carrier means comprises carriers (20, 21, 22, 23) for the collimator plates (24, 25, 26, 27), an applicator frame (18) mounting said carriers for movement perpendicularly to the direction of the symmetry axis (13), said frame being constructed for insertion into an accessory holder (7) of the electron source (2).

6. An electron applicator according to claim 1, characterized in two edges of each wall element (28, 29, 30, 31) being curved in on the side remote from the electron source and facing the symmetry axis (13), and terminating essentially flush with the respective collimator plate (24, 25, 26, 27) each wall element being fixedly connected with the respective colimator plate (24, 25, 26, 27) for reinforcing collimation of the cone of rays (14).

7. An electron applicator according to claim 5, characterized in that the frame (18) is provided with a coding means (63-65) characterizing the maximum width of the electron applicator (15).

8. An electron applicator according to claim 5, characterized in that the frame (18) is provided with a coding means (63-65) characterizing the respective positions of the collimator plates (24, 25, 26, 27) of the electron applicator (15).

9. An electron applicator according to claim 8, characterized in that the coding means (63-65) of the frame (18) has information transmission means (76-83) for readoff therefrom, arranged on the accessory holder (7).

10. An electron applicator according to claim 5, characterized in that the frame (18) carries potentiometers (63, 64, 65) coupled with adjustment mechanism (57, 58, 59; 60, 61, 62; 66, 67) of the individual collimator plates (24, 25, 26, 27), and that contacts (68 through 75) are provided on the accessory holder (7) which, when the frame (18) is inserted, can be brought into contact with the potentiometers, said contacts being connected with corresponding control circuits of the primary field shaping means (12).

11. An electron applicator according to claim 10, characterized in that the control circuits release the radiation only when the positions of the primary field shaping means (9, 10, 11) coincide with the positions of the corresponding collimator plates (24, 25, 26, 27) of the electron applicator (15).

12. An electron applicator tube according to claim 10, characterized in that the control circuits each comprise a follow-up control, respectively, which adjust the individual field shaping means of the electron source in accordance with the positions of the corresponding collimator plates of the electron applicator.

* * * * *